United States Patent [19]

Ralph

[11] Patent Number: 5,683,393

[45] Date of Patent: Nov. 4, 1997

[54] BIDIRECTIONAL ROD-HOOK LOCKING MECHANISM

[75] Inventor: James D. Ralph, Oakland, N.J.

[73] Assignee: Third Millennium Engineering, LLC, Summit, N.J.

[21] Appl. No.: 772,409

[22] Filed: Dec. 23, 1996

[51] Int. Cl.⁶ ........................................... A61B 17/70
[52] U.S. Cl. ............................ 606/61; 606/73; 623/17
[58] Field of Search .......................... 623/16, 17, 18; 606/60, 61, 72, 73

[56] References Cited

U.S. PATENT DOCUMENTS

| | | | |
|---|---|---|---|
| 5,507,746 | 4/1996 | Lin | 606/73 X |
| 5,527,314 | 6/1996 | Brumfield et al. | 606/61 |
| 5,562,661 | 10/1996 | Yoshimi et al. | 606/61 |
| 5,601,552 | 2/1997 | Cotrel | 606/61 |
| 5,601,554 | 2/1997 | Howland et al. | 606/61 |

FOREIGN PATENT DOCUMENTS 9423660  10/1994  WIPO ........................... 606/61

*Primary Examiner*—Mary Beth Jones
*Attorney, Agent, or Firm*—Joseph P. Errico, Esq.

[57] ABSTRACT

A bidirectional rod locking mechanism for use with rod coupling elements of orthopaedic rod apparatus includes a rod coupling element having a hook-shaped rod receiving end and a threaded axial bore. The axial bore is disposed so close to the hook-shaped portion that the medial portion of the hole protrudes through the inner surface of the hook portion. A contoured threaded shaft is advanced into the bore such that the contoured medial portion thereof aligns with the inner surface of the hook to permit the receipt therein of a rod. The threadable translation of the shaft in the appropriate direction causes a misalignment of the contoured medial portion in a manner which prevents the rod from being removed from the hook-shaped receiving locus.

6 Claims, 1 Drawing Sheet

BIDIRECTIONAL ROD-HOOK LOCKING MECHANISM

BACKGROUND OF THE INVENTION

1. Field of the Invention

This invention relates generally to a locking mechanism for securing a rod of an orthopaedic implant apparatus in a hook-shaped coupling element, and more specifically to a novel bidirectional interference locking mechanism.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape. In order to further strengthen such "rod assemblies", there have been developed a number of additional components, for example, cross-linking elements, which provide additional stability. Both the coupling elements of the screws as well as the additional supplemental elements must be secured to the rod. It is desirable that this mechanism be easy to affix and biomechanically strong.

Further, it has been recognized that rod coupling features of these implant devices should be positioned as close to the bone surface as possible to avoid continuous irritation of the soft tissues, i.e., muscles, nerves, blood vessels, skin, etc. It has therefore been a design goal for advanced coupling mechanisms to present as low a bone surface profile as is possible. Unfortunately, the goal has traditionally been one which runs counter to the goal of providing greater flexibility, i.e., polyaxialability, and strength.

It is, therefore, the principal object of the present invention to provide a rod coupling mechanism which provides ease of implantation.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

In addition, it is also a principle object of the present invention to provide a rod coupling mechanism which presents a very low profile relative to the natural anotomical bone surface to limit long-term soft tissue irritation.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a bidirectional interference looking mechanism for use with rod coupling hook-shaped elements. More particularly, a hook-shaped rod coupling element comprises a contoured member which receives a rod in the inner curvate portion thereof. In a coupling element utilizing the present invention comprises a threaded bore formed through a region of the portion of the element which is adjacent to the inner curvate surface thereof. The bore is sufficiently close to the hook shaped portion so that the medial portion of the bore forms an opening into the central portion of the hook shaped surface. The radius of the hook shaped surface is designed to be substantially equivalent to the curvature of the rod which is to be received in the hook.

A set screw, having a threaded cylindrical body and recessed end conformations to receive therein a screwdriving tool, is threadably advanced into the threaded bore prior to the positioning of a rod in the element. The set screw comprises an hourglass shaped locking shaft, having threading provided on the upper and lower portions thereof. The axial curvature of the medial portion (i.e., the inwardly tapered portion) of the hourglass shaped locking shaft is substantially equivalent to the missing curvature of the surface of the hook shaped portion. Thus, when the locking shaft is disposed in the bore, such that the medial portion of the locking shaft is aligned properly relative to the opening in the surface of the hook shaped portion, the curvature of the inner surface of the hook is constant and a rod of proper size may be placed in the hook shaped portion. Once placed therein, however, rotational advance of the locking shaft in the bore causes an offset of the surfaces of the locking shaft and the hook shaped portion, such that an interference lock may be provided against the rod, thereby holding the rod in the hook shaped portion. It shall be understood that the bidirectionality of this set screw is provided insofar as it may be accessed and operationally engaged at either end thereof, at either end of the bore. The direction of advancement which provides the locking action is not bidirectional, only one directional of translation will secure the rod in the hook.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
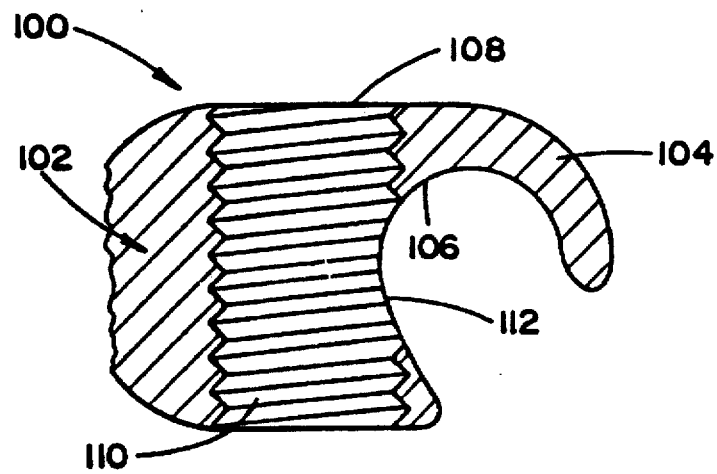
FIG. 1 is a side cross-section view of a rod coupling element of the present invention.

Referring now to FIG. 1, the present invention is directed to a locking mechanism for use with hook-shaped rod coupling elements such as the one illustrated in a side cross-section. More particularly, the operational portion 100 of such a rod coupling element shown herein includes a first end 102 which may be integrally formed with any implant device which requires fixation to a rod, such as rigid, or polyaxial, pedicle screws or cross-link devices. The portion 100 further includes a second end 104, having a hook-shaped cross-sectional conformation. The interior surface 106 of said hook-shaped end 104 is ideally suited to the dimensions of the rod which is to be placed therein, i.e. the radius of curvature of the inner surface 106 is constant and equal to that of the rod. The cross-sectional arc of the section 104 is approximately 180 degrees so that the rod can just slip in.

The intermediate portion 108 of the hook-shaped element comprises a threaded bore 110 which extends through the element at an approxiamtely perdendicular direction to the axes of the rod which would be placed in the hook end 104 and the elongate axis of the element 100 itself. This bore 110 is disposed sufficiently close to the hook end 104 that a medial portion of the bore 110 extends through the inner surface 106 of the hook end 104, such that there is a hole 112 formed in the otherwise constant radius rod receiving site.

Figure 2:
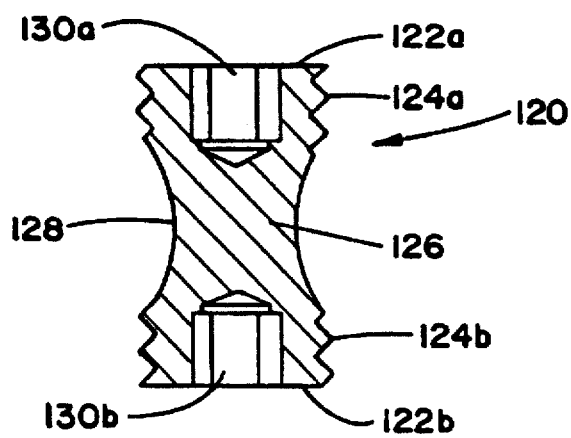
FIG. 2 is a side view of a bidirectional set screw of the present invention.

Referring now also to FIG. 2, a hourglass shaped shaft 120 is provided to be positioned in the bore 110 of the rod coupling element 100. More specifically, the shaft comprises constant diameter upper and lower portions 122a,122b, respectively. These upper and lower portions 122a,122b include threadings 124a,124b respectively. These threadings are intended to engage the threads of the bore 110 at upper and lower portions thereof. The diameter of the upper and lower portions 122a,122b are correspondingly substantially equivalent to the diameter of the bore 110; and the threadings 124a,124b comprise a single, broken, helical pattern such that the entire shaft may be advanced into the bore 110 without crossthreading.

The medial portion 126 of the shaft 120 comprises an hourglass conformation as it has a concavely tapered axial conformation 128. This concave axial taper 128 comprises approximately the curvature of the missing portion of the inner surface 106 of the hook portion 104 of the rod coupling element 100. Stated equivalently, the axial conformation 128 of the hourglass-shaped medial portion 126 of the shaft 120 is provided to match the curvature of the hook 104 when the shaft 120 is initally aligned in the bore 110.

In addition, the shaft 120 includes recesses 130a,130b at each axial end; said recesses being provided so that the shaft may be engaged by a screwdriving tool at either end.

Figure 3:
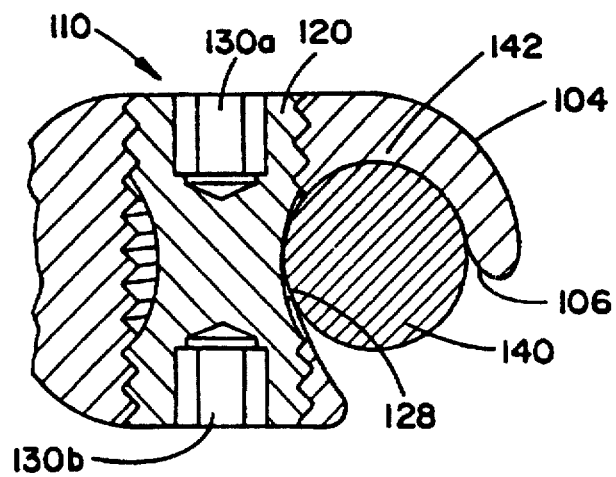
FIG. 3 is a side cross-section view of a fully assembled coupling element which includes an embodiment of the present invention.

Referring now to FIG. 3, the fully assembled coupling mechanism is provided in cross-section, with a rod 140 inserted into the hook end 104 thereof. During assembly, the shaft 120 is inserted in the bore 110 until the missing curvate portion of the inner surface 106 of the hook end 104 is replaced by the concave axial taper 128 of the shaft 120. Once this shaft 120 is properly positioned, the rod 140 may be received by and fully nested within the hook-shaped end 104. Once it is so placed, the shaft 120 is engaged by a screwdriving tool at either recess 130a or 130b, and rotationally translated toward the base 142 of the hook end 104 (in the orientation provided in FIG. 3, the direction is up). By advancing the shaft 120 in the bore 110 in this manner, the surface 128 of the shaft 120 becomes misaligned relative to the interior surface 106 of the hook 104 in such a way as to securely compress the rod 140 within the hook 104 via an interference crushing force. It shall be understood that while the shaft 120 may be engaged from either end, the locking direction is unique.

While there has been described and illustrated a preferred embodiment of a rod locking mechanism for use with various elements of posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

I claim:

1. A rod locking mechanism for use with orthopedic rod implantation apparatus, comprising:

a rod coupling element having
a hook-shaped end defining an interior curvate surface for receiving therein a rod of said orthopaedic rod implantation apparatus,
an intermediate portion which is adjacent to said hook-shaped end, and
a bore extending through said intermediate portion such that an axially medial portion of said bore forms a hole in said interior curvate surface of said hook-shaped end; and
a shaft having a curvate tapered medial portion, said curvate taper having a substantially equivalent radius of curvature as the interior curvate surface of the hook-shaped end at the hole formed therein by the bore such that when the shaft is aligned within said bore, said curvate tapered medial portion thereof provides a continuous surface of equivalent curvature at the hole formed in the interior curvate surface, and said shaft being selectably translatable within said bore such that when a rod has been received within said hook-shaped end, said shaft may be translated to an alternate position such that said curvate tapered medial portion thereof is no longer continuously aligned with said curvate interior surface, thereby interference locking said rod within the hook-shaped end.

2. The mechanism as set forth in claim 1, wherein said bore is threaded, and said shaft has a corresponding threading on upper and lower portions thereof such that said shaft may be selectively translated within said bore via rotation of the shaft.

3. The mechanism as set forth in claim 2, wherein said curvate tapered medial portion of said shaft is circumferentially symmetric.

4. The mechanism as set forth in claim 2, wherein said shaft further comprises recesses formed in first and second axial ends thereof, such that said shaft may be rotationally operated from either end, through either end of the bore.

5. The mechanism as set forth in claim 1, wherein said bore is oriented perpendicularly to the axis of the rod when said rod is appropriately seated in said hook-shaped end.

6. The mechanism as set forth in claim 1, wherein the interior curvate surface and said curvate tapered medial portion of said shaft comprise equivalent and constant radii of curvatures.

* * * * *